United States Patent [19]

Suzuki et al.

[11] 4,238,406

[45] Dec. 9, 1980

[54] METHOD FOR PREPARING A MIXTURE OF STEREOISOMERS OF α-CYANO-3-PHENOXYBENZYL 2-(4-CHLOROPHENYL)ISOVALERATE

[75] Inventors: Yukio Suzuki; Kohichi Aketa, both of Toyonaka; Masachika Hirano, Ibaraki, all of Japan

[73] Assignee: Sumitomo Chemical Company, Limited, Osaka, Japan

[21] Appl. No.: 7,536

[22] Filed: Jan. 29, 1979

[30] Foreign Application Priority Data

Jan. 27, 1978 [JP] Japan .................................... 53-8621

[51] Int. Cl.$^3$ ....................... C07C 121/75; A01N 9/20
[52] U.S. Cl. .................................. 260/465 D; 424/304
[58] Field of Search .................................... 260/465 D

[56] References Cited

U.S. PATENT DOCUMENTS

| 3,996,244 | 12/1976 | Fujimoto et al. | 260/332.2 A |
| 4,133,826 | 1/1979 | Warnant et al. | 260/465 D |
| 4,151,195 | 4/1979 | Warnant et al. | 260/465 D |

FOREIGN PATENT DOCUMENTS 857859 12/1977 Belgium .
54-109945 8/1979 Japan .

OTHER PUBLICATIONS

Elliott et al., *Pestic. Sci.*, vol. 9, pp. 105–111 (1978).
Elliott et al., *Nature*, vol. 248, pp. 710–711 (1974).
Aketa et al., *Agric. Biol. Chem.*, vol. 42(4), pp. 895–896 (1978).

*Primary Examiner*—Dolph H. Torrence
*Attorney, Agent, or Firm*—Sughrue, Rothwell, Mion, Zinn and Macpeak

[57] ABSTRACT

An α-cyano-3-phenoxybenzyl 2-(4-chlorophenyl)isovalerate which consists substantially of or is rich in (S)-α-cyano-3-phenoxybenzyl (S)-2-(4-chlorophenyl)isovalerate and (R)-α-cyano-3-phenoxybenzyl (R)-2-(4-chlorophenyl)isovalerate. A method for preparing the same and an insecticidal and acaricidal composition.

21 Claims, No Drawings

METHOD FOR PREPARING A MIXTURE OF STEREOISOMERS OF α-CYANO-3-PHENOXYBENZYL 2-(4-CHLOROPHENYL)ISOVALERATE

BACKGROUND OF THE INVENTION

1. Field of the Invention

This invention relates to an α-cyano-3-phenoxybenzyl 2-(4-chlorophenyl)isovalerate having a higher insecticidal and acaricidal activity, a process for preparing the same, and an insecticidal and acaricidal composition. More particularly, the present invention relates to an α-cyano-3-phenoxybenzyl 2-(4-chlorophenyl)isovalerate which consists substantially of or is rich in (S)-α-cyano-3-phenoxybenzyl (S)-2-(4-chlorophenyl)isovalerate and (R)-α-cyano-3-phenoxybenzyl (R)-2-(4-chlorophenyl)isovalerate.

2. Description of the Prior Art

α-Cyano-3-phenoxybenzyl 2-(4-chlorophenyl)isovalerate of the formula (I):

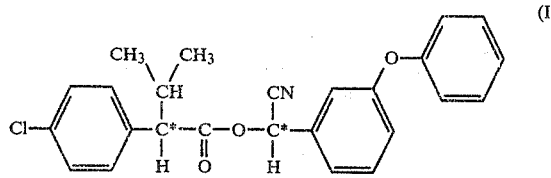

has a low toxicity to mammals and a broad range of insecticidal activity (e.g., as disclosed in Japanese Patent Application (OPI) No. 26425/74[the term "OPI" as used herein refers to a "published unexamined Japanese patent application"], and U.S. Pat. No. 3,996,244) the compound contains two asymmetric carbon atoms in the molecule (designated by an asterisk (*) in formula (I)) and, therefore, includes four optical isomers.

In this specification, α-cyano-3-phenoxybenzyl 2-(4-chlorophenyl)isovalerate and its isomers will be identified as follows: α-cyano-3-phenoxybenzyl 2-(4-chlorophenyl)isovalerate of the formula (I) above will be referred to hereinafter as "fenvalerate", (R, S)-α-cyano-3-phenoxybenzyl (S)-2-(4-chlorophenyl)isovalerate will be referred to as "fenvalerate A", (S)-α-cyano-3-phenoxybenzyl (S)-2-(4-chlorophenyl)isovalerate will be referred to as "fenvalerate Aα", (R)-α-cyano-3-phenoxybenzyl (S)-2-(4-chlorophenyl)isovalerate will be referred to as "fenvalerate Aβ", (S)-α-cyano-3-phenoxybenzyl (R)-2-(4-chlorophenyl)isovalerate will be referred to as "fenvalerate Bα", (R)-α-cyano-3-phenoxybenzyl (R)-2-(4-chlorophenyl)isovalerate will be referred to as "fenvalerate Bβ", the mixture of fenvalerate Aβ and fenvalerate Bα will be referred to as "fenvalerate X", and the mixture of fenvalerate Aα and fenvalerate Bβ will be referred to as "fenvalerate Y".

The relationship between the absolute configurations of the asymmetric carbon atoms on the acid moiety and alcohol moiety to the insecticidal activity of the compounds has already been reported. The following references describe fenvalerate Aα, having S-configurations at the asymmetric carbon atoms on both acid and alcohol moieties, as the most active stereoisomer of the four. See Miyakado et al., *Agr. Bio. Chem.*, 39, 267 (1975); Japanese Patent Application (OPI) No. 24019/78 (corresponding to U.S. Ser. No. 825,570, filed Aug. 17, 1977); Japanese Patent Application (OPI) No. 59646/78; Ohno et al., *J. Pesticide Science*, 2 (Special Issue), December 1977; and Aketa et al., *Agr. Bio. Chem.*, 42, 895 (1978).

In the case of esters of α-cyano-3-phenoxybenzyl alcohol and a dihalovinylcyclopropanecarboxylic acid, for example, cypermethrin (NRDC-149), i.e., α-cyano-3-phenoxybenzyl 2,2-dimethyl-3-(2,2-dichlorovinyl)cyclopropanecarboxylate, and α-cyano-3-phenoxybenzyl 2,2-dimethyl-3-(2,2-dibromovinyl)-cyclopropanecarboxylate, the S-isomers of the alcohol moiety in the esters are more active than the R-isomers thereof. Racemization (or epimerization) of α-cyano-3-phenoxybenzyl esters of d-cis-2,2-dimethyl-3-(2,2-dibromovinyl)-cyclopropanecarboxylic acid and d-cis-2,2-dimethyl-3-(2,2-dichlorovinyl)-cyclopropanecarboxylic acid in the presence of a basic catalyst has been reported and, furthermore, S-isomer esters of the alcohol moieties have been obtained from the ester having RS-alcohol and d-cis isomer of these dihalovinylcyclopropanecarboxylic acids as described in Belgian Patent No. 853,866 (1977) and Belgian Patent No. 853,867 (1977).

Although these patents claim the "chiral acid" ester in the examples, only cases of d-cis-dihalovinylcyclopropanecarboxylic acid esters are shown. Particularly, in the latter case, one stereoisomer must crystallize selectively from the solution of the mixture with the enantiomer; therefore every "chiral acid" ester isomer cannot be obtained.

In the case of fenvalerate, the epimerization of the alcohol moiety of the optically active fenvalerate and the processes for obtaining fenvalerate Aα from fenvalerate A by a selective crystallization or crystallization combined with simultaneous epimerization have been applied for in U.S. application Ser. No. 922,476, filed July 7, 1978 (corresponding to British Application No. 29,114/78). However, in these methods for obtaining fenvalerate, the optical resolution of the carboxylic acid is necessary, for example, these methods involve the reaction with an optically active base, the selective crystallization of a diastereomer salt, the purification of the salt and the decomposition of the salt. Furthermore, the enantiomeric acid by-product must be reused, for example, after racemization. On the other hand, the racemization of the useful acid or derivatives thereof must be avoided and, as a result, the reaction conditions are limited.

SUMMARY OF THE INVENTION

This invention in one embodiment provides a new stereoisomer mixture of fenvalerate, i.e., "fenvalerate Y". Fenvalerate Y's insecticidal and acaricidal activities are higher than fenvalerate which is prepared by common procedures.

This invention in another embodiment provides a process for preparing fenvalerate Y or fenvalerate Y-rich fenvalerate.

An insecticidal composition comprising fenvalerate Y or fenvalerate Y-rich fenvalerate as an active ingredient possesses an unexpectedly high insecticidal and acaricidal activity, and it can be used practically.

DETAILED DESCRIPTION OF THE INVENTION

The present invention provides a process for preparing fenvalerate Y which comprises precipitating the crystals of fenvalerate Y from a fenvalerate solution in the presence or absence of a basic catalyst; or for preparing a fenvalerate Y-rich fenvalerate which comprises precipitating crystals of fenvalerate Y in the presence of a basic catalyst and then concentrating the resulting crystal-containing slurry as it is or after removal or deactivation of the catalyst.

The present invention provides a method for precipitating fenvalerate Y as crystals from fenvalerate without a catalyst (referred to as "method A" hereinafter). In another case, a fenvalerate X-rich mother liquor, which has been separated from the fenvalerate Y crystals, is brought into contact with a basic catalyst, thereby epimerizing the alcohol moiety until the ratio of fenvalerate X to fenvalerate Y reaches equilibrium, and then the crystallization operation is carried out again. Thus, fenvalerate can finally be converted to fenvalerate Y almost quantitatively (hereafter referred to as "method A'"). By the methods A and/or A', fenvalerate containing practically no fenvalerate X can be obtained.

In method A, as raw material fenvalerate, one can use the fenvalerate Y-rich fenvalerate which can be prepared, for example, by method C described below. In method A, fenvalerate Y can be prepared in a good yield corresponding to the fenvalerate Y content of the fenvalerate starting material. Further, in the crystallization of fenvalerate Y according to method A, the present invention also provides a method which comprises carrying out the crystallization in the presence of a basic catalyst (referred to as "method B" hereinafter). The basic catalyst acts to epimerize the asymmetric carbon atom in the alcohol moiety. By adding this catalyst to the crystallization system of fenvalerate Y, it becomes possible to prepare fenvalerate Y crystals in amounts larger than that initially contained in the fenvalerate. The reason for this is considered as follows: The ratio of fenvalerate Y to fenvalerate X in the mother liquor decreases to less than equilibrium by crystallization of fenvalerate Y, and the decrement of fenvalerate Y is compensated by epimerization of fenvalerate X to fenvalerate Y in the mother liquor. As a result, whereas method A theoretically produces fenvalerate Y crystals in an amount of 50 parts, and generally only 20 to 30 parts, upon crystallization from 100 parts of raw fenvalerate, method B produces 40 to 80 parts or more fenvalerate Y crystals from 100 parts of raw fenvalerate.

Further, the present invention provides a method for preparing a fenvalerate Y-rich fenvalerate mixture which comprises concentrating the mother liquor together with fenvalerate Y obtained by the method B (referred to as "method C" hereinafter). In method B, the fenvalerate in the mother liquor separated from the fenvalerate Y crystals by filtration or the like naturally contains about half the amount of fenvalerate Y. If fenvalerate in the mother liquor recovered in method B is reused as a starting material for method B, loss in amount naturally becomes small, but this method is not practical considering that the impurities are increasingly concentrated.

Method C recovers the fenvalerate of the mother liquor together with fenvalerate Y crystals thereby making effective use of fenvalerate Y contained in the mother liquor. Simple concentration after crystallization is easy but the catalyst remains, and, therefore, attention should be given to the danger that the fenvalerate Y is isomerized into fenvalerate by epimerization by the action of the remaining catalyst. This danger can be avoided by deactivating the catalyst with addition of an acidic substance prior to concentration, but the catalyst components still remain in the product. When the catalyst or its deactivated product is insoluble, it can be removed by filtration and the like. When it is water-soluble, it can be conveniently removed by washing it with water as it is when the solvent is water-insoluble, or by adding a water-insoluble solvent followed by washing with water when the solvent is water-soluble. Alternatively, it may be possible to precipitate fenvalerate Y as crystals and then to use the resulting slurry for preparation as it is or after mere deactivation of the catalyst.

According to the method C, as described above, it is possible to convert racemic fenvalerate originally comprising 45 to 50 parts of fenvalerate Y and 55 to 50 parts of fenvalerate X into fenvalerate Y-rich fenvalerate almost quantitatively.

In accordance with the present invention it has been found that fenvalerate Y (m.p. 40° C.) crystallizes and can be selectively crystallized from the fenvalerate solution. As shown in the following examples, this crystallization from the solution of fenvalerate proceeds very slowly. Fenvalerate Y has never been refined. Fenvalerate Y-rich fenvalerate, in which the fenvalerate Y content is below 90%, has almost the same physical properties as fenvalerate prepared in common procedures and has never been crystallized.

Fenvalerate Y or fenvalerate Y-rich fenvalerate may be racemic or optically active, and the fenvalerate as the raw material need not be optically active.

As is the case with other pyrethroid-type esters, the crystallization of the above compound is not apparent and cannot be realized from the properties of racemic fenvalerate which is a viscous oily substance. For example, α-cyano-3-phenoxybenzyl 2,2-dimethyl-3-(2,2-dichlorovinyl)-cyclopropanecarboxylate, which is a pyrethroid-type ester having the same alcohol moiety as the above compound, no ester thereof having a d-trans (1R, 3S) acid moiety and an (S), (R) or racemic alcohol moiety has been known to crystallize. However, both a 1:1 (by weight) mixture (m.p. 75.0°–76.8° C.) of an ester having a d-trans acid moiety and an (R) alcohol moiety and an ester having an l-trans (1S, 3R) acid moiety and an (S) alcohol moiety and a 1:1 (by weight) mixture (m.p. 78.5°–80° C.) of an ester having a d-trans acid moiety and an (S) alcohol moiety and an ester having an l-trans acid moiety and an (R) alcohol moiety have been obtained as crystals.

It has also been found that in α-ethynyl-3-phenoxybenzyl 2-(4-chlorophenyl)isovalerate, which is a pyrethroid-type ester having a very similar chemical structure to the above compound, a mixture (m.p. 46°–47° C.) of esters having a racemic acid moiety and a racemic alcohol moiety, a mixture of two diastereomers thereof (each being racemic), and an ester thereof having an optically active acid moiety are crystalline at room temperature. When the ester mixture having a racemic acid moiety and a racemic alcohol moiety is recrystallized from hexane, a diastereomer having a melting point of 87° to 88° C. and a very weak insecticidal activity crystallizes predominantly. The ester recovered from the mother liquor is a diastereomer (m.p. 51°–52° C.) having a higher insecticidal activity. On the other hand, when the ester having an optically active acid moiety (m.p. 61°–62° C.) is subjected to this procedure, selective crystallization of a diastereomer is not observed, and no single stereoisomer is crystallized.

In allethrin (i.e., allethronyl chrysanthemate) a well known synthetic pyrethroid-type ester which includes four diastereomers, only a diastereomer ("crystalline allethrin") consisting of an ester having a d-trans acid moiety and an l-alcohol moiety and an ester having an l-trans acid moiety and a d-alcohol moiety is known to crystallize (e.g., as disclosed in M. Matsui & I. Yamamoto, *Natural Occurring Insecticides*, M. Jacobson & D. G. Grosby Eds., pp. 38–42, Marcel Dekker, Inc., New York (1971)). No enantiomorph of "crystalline allethrin" is known to crystallize by itself.

These facts show that it is quite impossible to predict which optical isomers or mixtures thereof can be obtained as crystals, and that even when a certain optical isomer is obtained as a crystal, it is quite impossible to predict whether that optical isomer can be selectively crystallized from a mixture of that optical isomer with other optical isomers.

Fenvalerate Y is a mixture which comprises fenvalerate Aα and fenvalerate Bβ, and the melting point is lower than that of fenvalerate Aα. Furthermore, the solubilities of fenvalerate Y are larger than those of fenvalerate Aα. Therefore, the crystallization condition of fenvalerate Y is more restricted than fenvalerate Aα.

In the methods of the present invention, it is not always necessary that the acid moiety or alcohol moiety of the raw fenvalerate forms a racemate, and the fenvalerate Y produced is not always a racemate. In the methods B and C of the present invention, there is of course no limitation on the weight ratio of fenvalerate X to fenvalerate Y in the raw fenvalerate. In method A, fenvalerate Y-rich fenvalerate can be used to obtain fenvalerate Y.

In carrying out the present invention, a solvent is generally used since fenvalerate is a liquid having little or no fluidity at crystallization temperature. The solvent is not particularly limited if fenvalerate and fenvalerate X are suitably soluble in it but fenvalerate Y is hardly soluble in it. As the solvent, there may be given, for example, hydrocarbon solvents (e.g., hexane, heptane, methylcyclohexane, etc.) and lower alcohols (e.g., methanol, ethanol, etc.). Lower alcohols are preferred, and of the lower alcohols, methanol is particularly preferred. Other preferred solvents are the mixture of a lower alcohol, preferably methanol, and an aliphatic or alicyclic hydrocarbon, such as hexane, heptane or methylcyclohexane. Other solvents such as aromatic hydrocarbons (e.g., benzene, toluene, monochlorobenzene, xylene, etc.) can be used in admixture with the alicyclic or aliphatic hydrocarbon but not in amounts larger than the aliphatic or alicyclic hydrocarbon. The concentration of fenvalerate is optionally selected within the range of 1 to 95% by weight, but concentrations of 20 to 80% by weight are preferred.

For the purpose of crystallization, it is desirable to add seed crystals. A preferred seed crystal is the crystal of fenvalerate Y, but the crystal of fenvalerate Aα or fenvalerate Bβ, or a mixture of both crystals in optional proportions may also be used satisfactorily. The amount of seed crystal is not particularly limited, but the crystallization or reaction is faster with a large amount of seed crystals, preferably an amount greater than 5% based on the fenvalerate in the solution. Therefore, in the method B or C, it is better to perform the step of crystallization with epimerization continuously or semi-continuously.

In the method A', epimerization of the fenvalerate X-rich fenvalerate in the mother liquor separated from fenvalerate Y crystals, can be achieved by contacting the fenvalerate solution with a basic catalyst. Any solvent may be used for this reaction, if it can dissolve fenvalerate and it does not decompose or form impurities by reaction with the fenvalerate or catalyst. Suitable solvents include, for example, methanol, ethanol, ethyl acetae, toluene, hexane, chloroform, acetonitrile, ethyl ether and the like.

The catalyst may be optionally selected from basic substances such as nitrogen-containing bases, phosphorus-containing bases, metal oxides, metal hydroxides, salts of metals with weak acids such as carbonic acid, silicic acid or hydrocyanic acid, and base-type ion exchange resins. Specific examples of catalysts which can be used include ammonia; aliphatic amines such as methylamine, ethylamine, n-propylamine, isopropylamine, n-butylamine, n-pentylamine, diethylamine, di-n-propylamine, di-n-butylamine, triethylamine, tri-n-propylamine, tri-n-butylamine, cyclohexylamine, and ethanolamine; aromatic amines such as aniline, 1-naphthylamine and 2-naphthylamine; quaternary ammonium salts such as tetramethyl ammonium hydroxide, tetraethyl ammonium hydroxide and tetra-n-propyl ammonium hydroxide; nitrogen-containing heterocyclic compounds such as pyridine; quinoline, pyrrolidine and piperidine; phosphorus-containing bases such as triphenyl phosphine and tri-n-butyl phosphine; metal oxides such as calcium oxide, magnesium oxide, beryllium oxide, zinc oxide, silicon dioxide and alumina; metal hydroxides such as sodium hydroxide, potassium hydroxide, magnesium hydroxide and calcium hydroxide; weak acid metal salts such as sodium carbonate, potassium carbonate, barium carbonate and potassium cyanide; talc; bentonite; the bases described above adsorbed on silica gel, alumina or activated carbon; and base-type ion exchange resins which have a basic group such as an amino group or a quaternary ammonium group. Suitable commercially available base-type ion exchange resins which can be used include "DOWEX 2×8" (a trademark for a product of the Dow Chemical Company, which is a strong base-type ion exchange resin made from a styrene-divinylbenzene copolymer having a quaternary ammonium group (—NR$_3$$^+$ +OH$^-$) incorporated therein), "AMBERLITE IR-45" (a trademark for a product of the Rohm & Haas Company, which is a weak base-type anion exchange resin having —N(R)$_2$, —NH(R) and —NH moieties as exchanging moieties), "AMBERLITE IRA-93" (a trademark for a product of the Rohm & Haas Company, which is a weak base-type anion exchange resin (MR-type) having an —N(CH$_3$)$_2$ moiety as an exchanging moiety), "AMBERLIST A-21" (a trademark for a product of the Rohm & Haas Company, which is a weak base-type anion exchange resin (MR-type) having an —N(CH$_3$)$_2$ moiety as an exchanging moiety and which is useful for non-aqueous solution), and "AMBERLIST A-27" (a trademark for a product of the Rohm & Haas Company, which is a strong base-type anion exchange resin (OH-type) having an

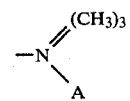

moiety as an exchanging moiety and which is useful for non-aqueous solutions).

From the standpoint of ease of removal of the catalyst after the epimerization reaction, those basic substances which are substantially insoluble in the solvents described above, especially base-type ion exchange resins, are preferred. It is to be understood that the basic catalyst is not limited to the materials exemplified hereinabove, and other substances can also be selected without departing from the spirit and scope of the invention.

In the method A', the catalyst may be added to the solution containing the fenvalerate X-rich fenvalerate to be epimerized, or the solution containing the fenvalerate X-rich fenvalerate may be passed through a column packed with the catalyst.

Suitable temperatures at which the epimerization can be accomplished are those at which the ester does not undergo any significant decomposition. The rate of epimerization is higher at higher temperatures. Preferably, the epimerization temperature ranges from about −50° C. to the boiling point of the solvent, more preferably from −20° C. to 150° C.

After epimerization is finished, removal of the catalyst and concentration of the solution are carried out, if necessary, and then the same crystallization as in the method A can be applied. The epimerization is carried out most easily, if the solvent is common to epimerization and crystallization.

As the basic catalyst used in the methods B and C there are nitrogen bases, phosphorus bases, quaternary ammonium hydroxides, metal-containing bases such as hydroxides, oxides, alcoholates, hydrides, carbonates, cyanides or amides of alkali metals (e.g., sodium, potassium, etc.) or alkaline earth metals (e.g., calcium, etc.), and basic ion-exchange resins. Of these basic catalysts, those which are soluble in the fenvalerate solution are preferred, and nitrogen bases such as ammonia and triethylamine are particularly preferred.

The amount of the basic catalyst based on fenvalerate is optionally selected within the range of 0.001 to 100 mole%. For weak bases such as nitrogen bases and phosphorus bases the range is preferably 1 to 100 mole%, while the amount is preferably 10 mole% or less for strong bases such as a quaternary ammonium hydroxide, sodium hydroxide, potassium hydroxide, sodium methylate and sodium hydride since decomposition takes place voluntarily.

In the present invention, crystallization temperatures lower than the melting point of fenvalerate Y are theoretically suitable, but preferably the temperature is 10° to −50° C., particularly −5° C. to −35° C.

In the method B or C, the basic catalyst must be removed from fenvalerate Y or fevalerate Y-rich fenvalerate obtained or neutralized. Otherwise, the ratio of fenvalerate X to fenvalerate Y can revert to about 50:50.

As is apparent from the aforesaid explanation, fenvalerate Y itself or fenvalerate Y-rich fenvalerate can be obtained from the commercially available racemic fenvalerate very simply and easily by the method of the present invention without applying troublesome methods such as optical resolution. Thus, the insecticidal activity of fenvalerate can be increased and, therefore, the method of the present invention is economically very important.

In practical application fenvalerate Y or fenvalerate Y-rich fenvalerate may be used alone or in combination with a carrier for convenience of use as a pesticide. The present compounds can be formulated into optional preparation forms without any special treating conditions according to the formulation of common pesticides. That is, the compounds may be formed into emulsifiable concentrates, wettable powders, dusts, granules, fine granules, oil sprays, aerosols, heating fumigants (mosquito coils, electric mosquito killers, etc.), thermal fogging agents, nonheating fumigants and baits by methods well known to those skilled in the art, and they may be used in forms which are suitable for application and in combination with a carrier.

Furthermore, the insecticidal activity of the present compounds can be increased by combination with known synergists for pyrethroid such as α-[2-(2-butoxyethoxy)ethoxy]-4,5-methylenedioxy-2-propyltoluene (hereinafter referred to as piperonylbutoxide), 1,2-methylenedioxy-4-[2-(octylsulfinyl)propyl]benzene (hereinafter referred to as sulfoxide), 4-(3,4-methylenedioxyphenyl)-5-methyl-1,3-dioxane (hereinafter referred to as sufroxane), N-(2-ethylhexyl)bicyclo[2,2,1]hepta-5-ene-2,3-dicarboximide (hereinafter referred to as MGK264), bis(2,3,3,3-tetrachloropropyl) ether (hereinafter referred to as S-421) and isobornylthiocyanoacetate (hereinafter referred to as Thanite); and with known synergists for allethrin or pyrethrins.

In general, the chrysanthemate type compounds tend to be inferior in resistance to light, heat and oxidation. Accordingly, it is recommended to add to the compositions of the present invention a proper amount of stabilizing agents, for example, antioxidants or UV absorbers such as phenol derivatives including BHT and BHA, bisphenol derivatives, arylamine derivatives including phenyl-α-naphthylamine, phenyl-β-naphthylamine and condensation products of phenetidine and acetone, and benzophenone compounds.

Additionally, the present compounds can be formulated into multipurpose compositions having more superior activity in combination with other active ingredients such as allethrin, N-(chrysanthemoxymethyl)-3,4,5,6-tetrahydrophthalimide (hereinafter referred to as tetramethrin), 5-benzyl-3-furylmethyl chrysanthemate (hereinafter referred to as Chrysron (a registered trademark of Sumitomo Chemical Co., Ltd.)), 3-phenoxybenzyl chrysanthemate, 5-proparylfurfuryl chrysanthemate and 2-methyl-5-propargyl-3-furylmethyl chrysanthemate, including, for example, d-trans- and d-cis,trans-chrysanthemic acid esters thereof, pyrethrum extracts, d-trans- or d-cis,transchrysanthemic acid esters of d-allethrolone, 3-phenoxybenzyl 2,2-dimethyl-3-(2,2-dichlorovinyl)cyclopropanecarboxylate, α-cyano-3-phenoxybenzyl 2',2'-dimethyl-3'-(2,2-dichlorovinyl)cyclopropanecarboxylate, α-cyano-3-phenoxybenzyl 2',2',3',3'-tetramethylcyclopropanecarboxylate, other well known cyclopropanecarboxylic acid esters; organophosphorus type insecticides such as, for example, O,O-dimethyl-O-(3-methyl-4-nitrophenyl)phosphorothioate (hereinafter referred to as Sumithion (a registered trademark of Sumitomo Chemical Co., Ltd.)). O,O-dimethyl-O-4-cyanophenyl-phosphorothioate (hereinafter referred to as Cyanox (a registered trademark of Sumitomo Chemical Co., Ltd.)), O,O-dimethyl-O-(2,2-dichlorovinyl)phosphate (hereinafter referred to as DDVP), O,O-dimethyl-O-4-methylmercapt-3-methylphenyl phosphorothioate, O,O-dimethyl-1-hydroxy-2,2,2-trichloroethyl phosphate, O,O-dimethyl-S-[1,2-bis(ethoxycarbonyl)ethyl]phosphorodithioate, 2-methoxy-4H-1,3,2-benzodioxaphospholin-2-sulfide, O,O-dimethyl-S-(1-ethoxycarbonyl-1-phenylmethyl)phosphorodithioate and O,O-diethyl-O-(2-isopropyl-4-methyl-6-pyrimidinyl)phosphorothioate; carbamate type insecticides such as, for example, 1-naphthyl-N-methylcarbamate, 3,4-dimethylphenyl-N-methylcarbamate (hereinafter referred to as Meobal, (a registered trademark of Sumitomo Chemical Co., Ltd.)), 3-methylphenyl-N-methylcarbamate, 2-isopropoxyphenyl-N-methylcarbamate and S-methyl-N-[(methylcarbamoyl)oxy]thioacetimidate, N'-(2-methyl-4-chlorophenyl)-N,N-dimethylformamidine, 1,3-bis(-carbamoylthio)2-(N,N-dimethylamino)propane hydrochloride; other insecticides, acaricides, fungicides, nematocides, plant growth regulators, microbial insecticides such as B.T. and B.M., insect hormone compounds, herbicides, fertilizers or other agricultural chemicals. Furthermore, a synergistic effect owing to the combination can also be expected.

In the following examples, the weight ratio of fenvalerate X to fenvalerate Y was measured by gas-chromatographic analysis. The analysis conditions were as follows:
Column: 10% Silicone DC-QF-1 (coated on Chromosorb AW-DMCS) 3mm$\phi \times$ 3.0 m
Analysis temperature: 245° C.
Injection temperature: 250° C.
Nitrogen pressure: 2.0 kg/cm$^2$
In the analysis under the above conditions, the retention times of fenvalerate X and fenvalerate Y were about 38 minutes and 43 minutes, respectively.

Unless otherwise indicated in the following examples, fenvalerate, fenvalerate X and fenvalerate Y refer to the racemates, and the weight ratio of fenvalerate X to fenvalerate Y in raw fenvalerate is 50:50.

EXAMPLE 1

5 g of fenvalerate (purity: 98.0%) was dissolved in 2.5 g of methanol, and 5 mg of fenvalerate Y crystals were added thereto. The solution was allowed to stand for 83 days in a refrigerator (about 0° C.). The weight of crystals collected by filtration was 1.0 g (yield 20%). The ratio of fenvalerate X to fenvalerate Y in the crystals was 1.0:99.0.

EXAMPLE 2

25 g of fenvalerate (purity: 98.0%) was dissolved in 25 g of methanol, and 10 mg of fenvalerate Y crystals were added thereto. The solution was stirred at 6° C. for 20 days. The weight of the crystals collected by filtration was 4.9 g (yield 20%). The ratio of fenvalerate X to fenvalerate Y was 4:96.

The weight of fenvalerate recovered by concentrating the mother liquor was 20.0 g, and the ratio of fenvalerate X to fenvalerate Y in the recovered fenvalerate was 63:37.

EXAMPLE 3

15 g of the fenvalerate recovered from the mother liquor in Example 2 was dissolved in 75 g of methanol. This solution was passed downward over 5 hours through a glass column packed with 100 cc of a basic ion-exchange resin (Amberlist A-21) slurried in methanol. Thereafter, 400 g of methanol was passed downward through the column over 3 hours. The eluates from the column were combined, and a part of the liquor was analyzed by gas chromatography. It was found that the ratio of fenvalerate X to fenvalerate Y was 53:47. The combined eluate was concentrated to a weight of 30 g under reduced pressure, and 10 mg of fenvalerate Y crystals were added thereto again. Crystallization was carried out at −6° C. for 20 days with stirring.

The weight of the crystals obtained was 2.3 g (yield 15%), and the ratio of fenvalerate X to fenvalerate Y was 4:96.

EXAMPLE 4

25 g of fenvalerate (purity: 98.0%) was dissolved in 50 g of methanol, and 0.12 g of a 28% aqueous ammonia solution and 10 mg of fenvalerate Y crystals were added thereto. The solution was stirred at −6° C. for 8 days.

The weight of fenvalerate Y crystals collected by filtration was 12.6 g (yield 50.4%). The ratio of fenvalerate X to fenvalerate Y was 1:99.

EXAMPLE 5

30 g of fenvalerate (purity: 98.0%) was dissolved in 15 g of methanol, and 0.3 g of triethylamine and 10 mg of fenvalerate Y crystals were added thereto. The solution was stirred at −6° C. for 7 days. To the resulting slurry were added 100 g of 0.2% hydrochloric acid and 40 g of toluene. The aqueous layer was separated and the oily layer was washed with water.

The oily layer was then concentrated under reduced pressure, and 29.7 g of fenvalerate having a fenvalerate X to fenvalerate Y ratio of 19:81 was recovered.

EXAMPLE 6

25 g of the fenvalerate (purity: 94.2%) having a fenvalerate X to fenvalerate Y ratio of 54:46 was dissolved in 50 g of methanol, and 0.75 g of triethylamine and 2.5 g of fenvalerate Y crystals were added thereto. The solution was stirred at −17° C. for 2 days.

To this slurry were added 100 g of 1% hydrochloric acid and 100 g of toluene, and the slurry was then separated into aqueous and oily layers. The oily layer was washed with water and concentrated to recover 24.5 g of fenvalerate having a fenvalerate X to fenvalerate Y ratio of 38:62.

EXAMPLE 7

40g of the fenvalerate used in Example 1 was dissolved in 80 g of methanol. Then, 3.1 g of methanol containing 10.5% of ammonia and 8 g of fenvalerate Y crystals were added thereto. The solution was stirred at −17° C. for 2 days. The weight of fenvalerate Y crystals collected by filtration was 36.4 g (yield 71%). The ratio of fenvalerate X to fenvalerate Y was 2.6:97.4.

EXAMPLE 8

40 g of the fenvalerate used in Example 6 was dissolved in 80 g of methanol. Then, 57 mg of sodium hydroxide dissolved in 2 g of methanol and 4 g of fenvalerate Y crystals were added thereto. After stirring at −17° C. for 3 days, 40 g of 5% hydrochloric acid and 40 g of toluene were added and the mixture was stirred at 20° to 25° C. After the aqueous layer was removed, the oily layer was washed twice with water. The toluene was distilled off under reduced pressure and 43.0 g of fenvalerate Y-rich fenvalerate (the ratio of fenvalerate X to fenvalerate Y: 13:87) was obtained.

EXAMPLE 9

40 g of the fenvalerate used in Example 6 was dissolved in 80 g of methanol. 0.36 g of a methanol solution containing 28% of sodium methylate and 4 g of fenvalerate Y crystals were added, and stirred at −17° C. After 3 days, 40 g of 5% hydrochloric acid and 40 g of toluene were added. The mixture was stirred at 20° to 25° C., the aqueous layer was removed, and the toluene layer was washed twice with water. The toluene was removed by distillation. 43.2 g of fenvalerate Y-rich fenvalerate (the ratio of fenvalerate X to fenvalerate Y: 14:86) was obtained.

EXAMPLE 10

40 g of the fenvalerate used in Example 6 was dissolved in 80 g of ethanol. Then, 1,5 g of a methanol solution containing 10.5% of ammonia and 4 g of fenvalerate Y crystals were added thereto. After stirring at −17° C. for 3 days, 40 g of 5% hydrochloric acid and 40 g of toluene were added and the mixture was stirred at 20° to 25° C. After the aqueous layer was removed, the oily layer was washed twice with water. The toluene was distilled off under reduced pressure. 42.7 g of fenvalerate Y-rich fenvalerate was obtained. The ratio of fenvalerate X to fenvalerate Y was 37.9:62.1.

EXAMPLE 11

40 g of the fenvalerate used in Example 6 was dissolved in a mixed solvent of 10 g of toluene and 70 g of n-heptane, and 4 g of fenvalerate Y crystals were added. At −17° C., stirring for 4 days, 40 g of 5% hydrochloric acid was added thereto and then stirred at 30° to 35° C. The aqueous layer was removed and the oily layer was washed with water. The toluene and n-heptane were distilled under reduced pressure, then 43.9 g of fenvalerate Y-rich fenvalerate whose ratio of fenvalerate X to fenvalerate Y was 31:69 was obtained.

EXAMPLE 12

40 g of the fenvalerate used in Example 9 was dissolved in a mixed solvent of 40 g of n-heptane and 32.3 g of methanol. Thereto, 7.7 g of methanol which contains 10.5% of ammonia and 4 g of fenvalerate Y crystals were added. After stirring at −17° C. for 3 days, 40 g of 5% hydrochloric acid and 20 g of toluene were added. The mixture was stirred at 20° to 25° C., the aqueous layer was removed and the oily layer was washed with water. The toluene and heptane were distilled off, then 43.3 g of fenvalerate Y-rich fenvalerate which contained fenvalerate X and fenvalerate Y in a weight ratio of 11:89 was obtained.

EXAMPLE 13

40 g of fenvalerate Y-rich fenvalerate, whose purity was 91.3% and the ratio of fenvalerate X to fenvalerate Y was 14.6:85.4, was dissolved in 80 g of methanol. The solution was cooled to 0° C., then 0.3 g of fenvalerate Y crystals were seeded. Under stirring, the mixture was cooled slowly to −15° C. for 3.5 hours, was then stirred at −15° to −16° C. for 2.5 hours. 28.2 g of the crystals were collected by filtration (yield: 69.8% by weight), whose ratio of fenvalerate X to fenvalerate Y was 3.8:96.2 and whose purity was 98.0%.

EXAMPLE 14

80 g of the fenvalerate Y-rich fenvalerate used in Example 13 was dissolved in 160 g of methanol and 0.1 g of fenvalerate Y crystals were added thereto. After stirring at −18° C. for 18 hours, the solution of 80 g of fenvalerate, whose purity was 92.0% and whose ratio of fenvalerate X to fenvalerate Y was 53.2:46.8, and 153.2 g of methanol was added to the mixture, then 6.2 g of a methanol solution of 10.5% of ammonia was added thereto. After further stirring for 24 hours, about half of the mixture was poured into a mixture of 80 g of toluene and 160 g of 1% hydrochloric acid, the oily layer was washed with water and the toluene was removed by distillation in vacuo. Thus, 82.58 g of the first fenvalerate Y-rich fenvalerate was obtained, whose ratio of fenvalerate X to fenvalerate Y was 17.4:82.6.

On the other hand, to the other half of the crystallization mixture, 80 g of fenvalerate, whose ratio of fenvalerate X to fenvalerate Y was 53.2:46.8, dissolved in 160 g of methanol was poured, and 3.1 g of a methanol solution of 10.5% ammonia was added thereto.

After stirring 24 hours, the same procedures were repeated and after an additional 24 hours of stirring the reaction was stopped completely by adding the mixture into 160 g of toluene and 320 g of 1% hydrochloric acid. The second and the third fenvalerate Y-rich fenvalerates were yielded in 81.0 g and 161.5 g, respectively, and their ratios of fenvalerate X to fenvalerate Y were 18.9:81.1 and 18.5:81.5, respectively.

Preparation of the insecticidal and acaricidal compositions in accordance with the present invention and lethal effect thereof will be illustrated with reference to the following preparation examples and test examples. All parts are by weight.

Preparation Example 1

0.2 part of fenvalerate Y or fenvalerate Y-rich fenvalerate was dissolved in kerosene to make total weight of 100 parts. Thus, oil sprays of each isomer were obtained.

Preparation Example 2

To 20 parts of fenvalerate Y or fenvalerate Y-rich fenvalerate were added 15 parts of Sorpol 3005X (a registered trademark of Toho Kagaku Co.) and 65 parts of xylene. The mixtures were each thoroughly mixed to make a solution. Thus, emulsifiable concentrates of each compound were obtained.

Preparation Example 3

To 10 parts of fenvalerate Y or fenvalerate Y-rich fenvalerate were added 20 parts of S-421, 15 parts of Sorpol 3005X (the same as above) and 55 parts of xylene. The mixtures were each thoroughly mixed to make a solution. Thus, emulsifiable concentrates to each isomer were obtained.

Preparation Example 4

0.1 part of the fenvalerate Y shown in Example 1, 0.2 part of tetramethrin, 7 parts of xylene and 7.7 parts of deodorized kerosene were mixed to make a solution. The solution was filled into an aerosol container. After attaching a valve portion to the container, 85 parts of a propellant (liquefied petroleum gas) was charged therein under pressure through the valve. An aerosol was thus obtained.

Preparation Example 5

0.15 g of fenvalerate Y or fenvalerate Y-rich fenvalerate and 0.2 g of d-trans acid isomer of allethrin were dissolved in 20 ml of methanol. The solutions were each uniformly mixed with 99.65 g of a mosquito coil carrier containing tabu-powder, pyrethrum murc and wood powder in a ratio of 3:5:2, and then the methanol was evaporated. To the residue obtained was added 150 ml of water and the mixture was kneaded thoroughly, shaped into a mosquito coil and dried. Thus, mosquito coils of each isomer were obtained.

Preparation Example 6

0.02 g of fenvalerate Y or fenvalerate Y-rich fenvalerate, 0.05 g of 5-propargyl-furfuryl dl-cis, transchrysanthemate and 0.1 g of BHT were dissolved in a suitable amount of chloroform. The solutions were each absorbed uniformly on filter paper of 3.5 cm×1.5 cm in size and 0.3 cm in thickness. Thus, fibrous heating fumigant insecticidal compositions for use on a heater were obtained.

Preparation Example 7

10 parts of fenvalerate Y or fenvalerate Y-rich fenvalerate, 20 parts of Sumithion (the same as above) and 5 parts of Sorpol SM-200 (a registered trademark of Toho Kagaku Co.) were thoroughly mixed. The mixtures were each mixed with 65 parts of 300 mesh diatomaceous earth in a mortar while thoroughly stirring. Thus, wettable powders of each compound were obtained.

Preparation Example 8

0.5 part of each of fenvalerate Y or fenvalerate Y-rich fenvalerate was dissolved in 200 parts of acetone, and then 99.5 parts of 300 mesh talc were added thereto. After thoroughly mixing in a mortar while stirring, the acetone was removed by evaporation. Thus, dusts were obtained.

Preparation Example 9

3 parts of each of fenvalerate Y or fenvalerate Y-rich fenvalerate, 5 parts of Toyolignin CT (a registered trademark of Toyo Spinning Co.) and 92 parts of GSM Clay (a registered trademark of Zieklite Mining Co.) were thoroughly mixed in a mortar.

Then, the mixtures were each mixed with water of 10% by weight based on the mixture, granulated by means of a granulator and air-dried. Thus, granular preparations were obtained.

Preparation Example 10

2 parts of each of fenvalerate Y or fenvalerate Y-rich fenvalerate, 2 parts of Cyanox, 5 parts of Toyolignin CT and 91 parts of GSM Clay were thoroughly mixed in a mortar.

Then, the mixtures were each mixed with water of 10% by weight based on the mixture, granulated by means of a granulator and air-dried. Thus, fine granular preparations of each compound were obtained.

Preparation Example 11

0.1 part of fenvalerate Y or fenvalerate Y-rich fenvalerate, 0.2 part of d-trans acid isomer of allethrin, 11.7 parts of deodorized kerosene and 1 part of Atmos 300 (an emulsifier (a registered trademark of Atlas Chemical Co.)) were thoroughly mixed and emulsified by an addition of 50 parts of distilled water. An aerosol container was then filled with the resulting emulsion and 35 parts of a 3:1 mixture of deodorized butane and deodorized propane. A water-based aerosol was thus obtained.

The insecticidal and acaricidal activities of the compositions thus obtained were tested as follows.

Test Example 1

Insecticidal activity on tobacco cut worm (*Spodoptera litura*)

Fenvalerate Y obtained in Example 4, fenvalerate Y-rich fenvalerate obtained in Examples 5 and 6 and common fenvalerate were formulated into a 20% emulsifiable concentrate as usual (Composition: above pesticide 20%; xylene 70%; and Sorpol 3005X (a registered trademark of Toho Kagaku Co.) 10%). These emulsifiable concentrates were each diluted with water to a pre-determined concentration, and mixed with a spreader (Shin-Rino, a registered trademark of Nippon Noyaku Co.) of 3,000 times by weight based on the diluted liquor.

Leaves were cut from a cabbage plant (prior to the head) cultivated in a flower pot, dipped in the above test solution for 1 minute and air-dried. The dried leaves were placed in a plastic cup (diameter 10 cm, height 4 cm) at a rate of 2 leaves/cup, and the fourth instar larvae of tobacco cut worms were liberated therein. The dead and alive were examined after 24 hours and the values of $LC_{50}$ (concentration required for 50% death) were obtained.

Experiments of three replications were carried out using 10 larvae per group. The results are shown in Table 1.

TABLE 1

| Insecticidal activity on tobacco cut worm | | | |
|---|---|---|---|
| Test Compound Example | Fenvalerate X:Y Ratio | $LC_{50}$ (ppm) | Relative* Efficacy |
| Example 4 | 1:99 | 3.8 | 195 |
| Example 5 | 19:81 | 4.3 | 172 |
| Example 6 | 38:62 | 5.9 | 125 |
| Fenvalerate (common product) | 52:48 | 7.4 | 100 |

*Activity of fenvalerate (common product) was taken as 100.

Test Example 2

Insecticidal activity on housefly (*Musca domestica*)

Each pesticide used in Examples 4 and 5 was diluted with acetone to a pre-determined concentration, and 0.5 μl of the solution was applied to the ventral thorax of CSMA-strain housefly female adults by means of a microsyringe. The adults were then liberated in a plastic cup (diameter 11 cm) wherein a bait (3% sugar water) was placed. The dead and alive were examined after 24 hours, and the values of $LD_{50}$ were obtained. The results are shown in Table 2.

TABLE 2

| Insecticidal activity on housefly | | | |
|---|---|---|---|
| Test Compound Example | Fenvalerate X:Y Ratio | $LD_{50}$ (μg/housefly) | Relative* Efficacy |
| Example 4 | 1:99 | 0.015 | 207 |
| Example 5 | 19:81 | 0.018 | 172 |
| Fenvalerate (common product) | 52:48 | 0.031 | 100 |

*Activity of fenvalerate (common product) was taken as 100.

Test Example 3

The insecticidal activity on housefly adults (*Musca domestica*) of the aerosols formulated according to the Preparation Examples 4 and 11 were tested by the aerosol test method (Soap and Chemical Specialities, Blue Book, 1965) using a (6 ft)³ Peet Grady's chamber. Thus, with any aerosol, more than 80% of the flies were knocked down within 15 minutes after spraying and more than 70% of the flies were killed by the next day.

Test Example 4

The dusts formulated according to Preparation Example 8 were applied to the potted rice plants 20 days after sowing in a proportion of 2 kg per 10 are by means of a Bell jar duster. Each pot was covered with wire net and about 20 adults of green rice leafhoppers (*Nephotettix cincticeps*) were liberated in the pot. After 24 hours, 100% of the leafhoppers were killed by the dusts.

Test Example 5

Carmine mite female adults (*Tetranychus cinnabarinus*) were made parastic on leaves of the potted kidney bean (primordial leaf-stage) which had grown 9 days since sowing, in a proportion of 10–15/leaf, and bred at 27° C. for a week in a constant temperature room. Then, numerous carmine mites were found to be bred at various growth stages. At this time, a 500 fold aqueous dilute solution of each emulsifiable concentrate formulated according to the Preparation Example 2 was sprayed in a proportion of 10 ml/pot on a turn-table. After 10 days, damage of kidney bean plants by the mites was hardly observed.

While the invention has been described in detail and with reference to specific embodiments thereof, it will be apparent to one skilled in the art that various changes and modifications can be made therein without departing from the spirit and scope thereof.

What is claimed is:

1. A method for preparing a mixture of (S)-α-cyano-3-phenoxybenzyl (S)-2-(4-chlorophenyl)isovalerate and (R)-α-cyano-3-phenoxybenzyl (R)-2-(4-chlorophenyl)isovalerate which comprises precipitating a mixture of (S)-α-cyano-3-phenoxybenzyl (S)-2-(4-chlorophenyl)isovalerate and (R)-α-cyano-3-phenoxybenzyl (R)-2-(4-chlorophenyl)isovalerate as crystals from a solution of α-cyano-3-phenoxybenzyl 2-(4-chlorophenyl)isovalerate, and separating the crystals from the mother liquor.

2. The method of claim 1, wherein said αcyano-3-phenoxybenzyl 2-(4-chlorophenyl)isovalerate used as a starting material contains more than 60% by weight (S)-α-cyano-3-phenoxybenzyl (S)-2-(4-chlorophenyl)isovalerate and (R)-α-cyano-3-phenoxybenzyl (R)-2-(4-chlorophenyl)isovalerate.

3. The method of claim 1, wherein said α-cyano-3-phenoxybenzyl 2-(4-chlorophenyl)isovalerate used as a starting material is prepared by precipitating a mixture of (S)-α-cyano-3-phenoxybenzyl (S)-2-(4-chlorophenyl)isovalerate and (R)-α-cyano-3-phenoxybenzyl (R)-2-(4-chlorophenyl)isovalerate as crystals from the solution of α-cyano-3-phenoxybenzyl 2-(4-chlorophenyl)isovalerate, separating the solution into the crystals and the mother liquor, and bringing α-cyano-3-phenoxybenzyl 2-(4-chlorophenyl)isovalerate in the separated mother liquor into contact with a basic catalyst to induce epimerization thereof.

4. The method of claim 3, wherein said basic catalyst is a base-type ion exchange resin.

5. The method of claim 3, wherein said basic catalyst is removed from the epimerized mother liquor, and the resulting mother liquor is concentrated.

6. A method for preparing a mixture of (S)-α-cyano-3-phenoxybenzyl (S)-2-(4-chlorophenyl)isovalerate and (R)-α-cyano-3-phenoxybenzyl (R)-2-(4-chlorophenyl)isovalerate which comprises precipitating a mixture of (S)-α-cyano-3-phenoxybenzyl (S)-2-(4-chlorophenyl)isovalerate and (R)-α-cyano-3-phenoxylbenzyl (R)-2-(4-chlorophenyl)isovalerate as crystals from a solution of α-cyano-3-phenoxybenzyl 2-(4-chlorophenyl)isovalerate in the presence of a basic catalyst.

7. A method for preparing α-cyano-3-phenoxybenzyl 2-(4-chlorophenyl)isovalerate which is rich in (S)-α-cyano-3-phenoxybenzyl (S)-2-(4-chlorophenyl)isovalerate and (R)-α-cyano-3-phenoxybenzyl (R)-2-(4-chlorophenyl)isovalerate, which comprises precipitating a mixture of (S)-α-cyano-3-phenoxybenzyl (S)-2-(4-chlorophenyl)isovalerate and (R)-α-cyano-3-phenoxybenzyl (R)-2-(4-chlorophenyl)isovalerate as crystals from the solution of α-cyano-3-phenoxybenzyl 2-(4-chlorophenyl)isovalerate in the presence of a basic catalyst, and recovering the crystals together with α-cyano-3-phenoxybenzyl 2-(4-chlorophenyl)isovalerate contained in the mother liquor.

8. The method of claim 6 or 7, wherein said basic catalyst is a nitrogen base.

9. The method of claim 8, wherein said nitrogen base is ammonia or triethylamine.

10. The method of claim 6 or 7, wherein said basic catalyst is selected from the group consisting of alkali metal hydroxides, alkaline earth metal hydroxides, alkali metal oxides, alkaline earth metal oxides, alkali metal amides, alkaline earth metal amides, alkali metal hydrides, alkaline earth metal hydrides, alkali metal alcoholates, and alkaline earth metal alcoholates.

11. The method of claim 10, wherein said basic catalyst is selected from the group consisting of alkali metal hydroxides and alkali metal alcoholates.

12. The method of claim 1, 3, 6 or 7, wherein precipitation of said crystals is carried out by adding seed crystals to the solution.

13. The method of claim 12, wherein the seed crystals are a crystal of a mixture of (S)-α-cyano-3-phenoxybenzyl (S)-2-(4-chlorophenyl)isovalerate and (R)-α-cyano-3-phenoxybenzyl (R)-2-(4-chlorophenyl)isovalerate.

14. The method of claim 13, wherein said seed crystals are present in an amount greater than 5% based on the α-cyano-3-phenoxybenzyl 2-(4-chlorophenyl)isovalerate in said solution.

15. The method of claim 1, 6 or 7, wherein precipitation of said crystals is carried out continuously or semi-continuously.

16. The method of claim 1, 3, 6 or 7, wherein said precipitation is carried out in a lower alcohol or mixed solvent thereof.

17. The method of claim 16, wherein said lower alcohol is methanol.

18. The method of claim 16, wherein a cosolvent is used with the lower alcohol.

19. The method of claim 18, wherein said cosolvent is an aliphatic or alicyclic hydrocarbon.

20. The method of claim 18, wherein said cosolvent is a mixture of an aliphatic or alicyclic hydrocarbon and an aromatic hydrocarbon, whose content is not larger than the aliphatic or alicyclic hydrocarbon.

21. The method of claim 19 or 20, wherein the aliphatic hydrocarbon is pentane, hexane, heptane or octane, and the alicyclic hydrocarbon is methylcyclohexane.

* * * * *